(12) United States Patent
McCallien et al.

(10) Patent No.: US 9,625,440 B2
(45) Date of Patent: Apr. 18, 2017

(54) METHOD OF MARKING HYDROCARBON LIQUIDS

(75) Inventors: Duncan McCallien, County Durham (GB); Vincent Brian Croud, South Yorkshire (GB)

(73) Assignee: JOHNSON MATTHEY PUBLIC LIMITED COMPANY, London (GB)

( * ) Notice: Subject to any disclaimer, the term of this patent is extended or adjusted under 35 U.S.C. 154(b) by 125 days.

(21) Appl. No.: 14/116,554

(22) PCT Filed: May 9, 2012

(86) PCT No.: PCT/GB2012/051016
§ 371 (c)(1),
(2), (4) Date: Dec. 12, 2013

(87) PCT Pub. No.: WO2012/153133
PCT Pub. Date: Nov. 15, 2012

(65) Prior Publication Data
US 2014/0087473 A1    Mar. 27, 2014

(30) Foreign Application Priority Data

May 11, 2011    (GB) .................................. 1107871.4

(51) Int. Cl.
| | | |
|---|---|---|
| *G01N 37/00* | (2006.01) | |
| *G01N 33/28* | (2006.01) | |
| *C10L 1/00* | (2006.01) | |
| *C10L 1/226* | (2006.01) | |

(52) U.S. Cl.
CPC .......... *G01N 33/2882* (2013.01); *C10L 1/003* (2013.01); *C10L 1/226* (2013.01); *Y10T 436/13* (2015.01)

(58) Field of Classification Search
None
See application file for complete search history.

(56) References Cited

U.S. PATENT DOCUMENTS

| | | |
|---|---|---|
| 4,009,008 A | 2/1977 | Orelup |
| 2005/0170976 A1 | 8/2005 | Lunt et al. |

FOREIGN PATENT DOCUMENTS

| | | |
|---|---|---|
| EP | 0509818 A1 | 10/1992 |
| EP | 1580254 A2 | 9/2005 |
| EP | 1580254 A3 | 11/2005 |
| WO | 9967346 A1 | 12/1999 |
| WO | 03078551 A2 | 9/2003 |

OTHER PUBLICATIONS

Mitchell, P.J. et al. 19F Nuclear Magnetic Resonance Studies of Aromatic Compounds. Part IV. Transmission of Substituent Effects across Two Aromatic Rings connected by an N—N Linkage, 1974, Royal Society of Chemistry, pp. 109-118.*
Abramovitch et al., "Solution and Flash Vacuum Pyrolyses of β-(3,5-Disubstituted-phenypethanesulfonyl Azides, Sultam, Pyrindine, and Azepine Formation", J. Org. Chem., 1984, vol. 49, No. 26, pp. 5124-5131.
GB Search Report, dated Sep. 9, 2011, from corresponding GB application.
International Search Report, dated Jul. 24, 2012, from corresponding PCT application.

* cited by examiner

*Primary Examiner* — Robert Xu
(74) *Attorney, Agent, or Firm* — Young & Thompson

(57) ABSTRACT

A method of marking a hydrocarbon liquid includes the step of

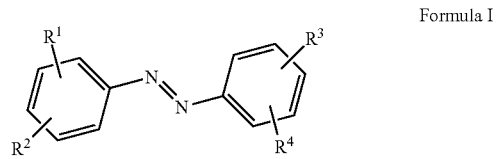

Formula I adding to the liquid, as a tracer compound, a compound of Formula I:
wherein at least one of $R^1$-$R^4$ is selected from:
  i. a bromine or fluorine atom;
  ii. a partially or fully halogenated alkyl group;
  iii. a branched or cyclic $C_4$-$C_{20}$ alkyl group;
  iv. an aliphatic substituent linking two positions selected from $R^1$-$R^4$ in Formula I to one another; or
  v. a phenyl group substituted with a halogen atom, an aliphatic group or halogenated aliphatic group. The tracer compounds are resistant to removal from the fuel by chemical laundering or by contact with absorbents such as charcoal.

7 Claims, No Drawings

METHOD OF MARKING HYDROCARBON LIQUIDS

The present invention concerns marking hydrocarbon liquids with tracer materials, in particular hydrocarbons which are taxable or liable to be subject to tampering or substitution such as gasoline and diesel fuels for example.

It is well known to add tracers to hydrocarbon liquids. A typical application is the tagging of hydrocarbon fuels in order to identify the liquid at a subsequent point in the supply chain. This may be done for operational reasons, e.g. to assist in distinguishing one grade of fuel from another, or for other reasons, in particular to ensure fuel quality, deter and detect adulteration and to provide a means to check that the correct tax has been paid. Apart from fuels, other products, such as vegetable oils may be marked to identify the product produced at a particular source, or certified to a particular standard.

One problem which is known to exist with the marking of fuel liquids in particular, is the potential for the tracer to be removed, by evaporation from the fuel, by degradation of the tracer through ageing or exposure to environmental conditions such as heat, sunlight or air or alternatively by deliberate removal of the tracer for unlawful purposes such as for avoidance of tax. Methods for deliberate removal of tracers include adsorption of the tracer onto common adsorbent materials such as charcoal or clays, exposure to radiation, such as ultraviolet light, oxidation etc. A useful fuel tracer therefore needs to be resistant to removal by these common methods and also to more sophisticated treatments such as treatment with acids and/or bases. It is an object of the invention to provide a method of marking hydrocarbon liquids which is more resistant to removal of the tracer than known methods.

EP 1580254 and EP 0509818 each describe hydrocarbon markers based on substituted bis(phenyl)diazine compounds in which at least one of the substituents on one of the aromatic rings is an OH group. This type of compound has been found to be less resistant to removal from hydrocarbons than the compounds used as tracers in the present invention. WO 99/67346 and WO 2003/078551 describe the use of substituted bis(phenyl)diazine compounds in which at least one of the substituents on one of the aromatic rings is a tertiary amino group. In each of WO 99/67346 and WO 2003/078551 the tracer compounds are designed to be extractable from hydrocarbons using a solution of an acid in order to detect the tracer compound. These compounds are therefore clearly not resistant to removal from hydrocarbon liquids using acid laundering methods in contrast to the tracers of the present invention.

According to the invention we provide a method of marking a hydrocarbon liquid comprising the step of adding to said liquid, as a tracer compound, a compound of Formula I:

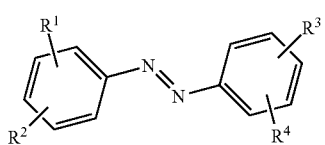

Formula I wherein at least one of $R^1$-$R^4$ is selected from:
i. a bromine or fluorine atom;
ii. a partially or fully halogenated alkyl group;
iii. a branched or cyclic $C_4$-$C_{20}$ alkyl group;
iv. an aliphatic substituent linking two positions selected from $R^1$-$R^4$ in Formula I to one another; or
v. a phenyl group substituted with a halogen atom, an aliphatic group or halogenated aliphatic group
and further wherein none of $R^1$-$R^4$ consists of a hydroxyl group or an amino group.

We further provide, according to the invention, a composition comprising a hydrocarbon liquid and a tracer compound, characterised in that said tracer compound tracer compound comprises a compound of Formula I, where Formula I is as described above.

We further provide, according to the invention, a method of identifying a hydrocarbon liquid comprising the steps of marking said liquid by the method of marking according to the invention, and subsequently analysing a sample of a hydrocarbon liquid for the presence of said tracer compound to determine whether said sample is a sample of said marked hydrocarbon liquid.

The hydrocarbon liquid may be a pure compound such as hexane or octane or it may comprise a mixture of compounds such as a distillation fraction having a particular range of boiling points. The hydrocarbon liquid may be intended for use as a chemical, a solvent or a fuel. In preferred embodiments the hydrocarbon liquid comprises a diesel fuel, a gasoline fuel or a solvent. The invention is of particular use for marking liquid hydrocarbon fuels such as gasoline and diesel fuels. In one particular application a low-tax fuel such as an agricultural diesel may be marked in order to detect any subsequent sale and use for purposes such as road-vehicle fuel which would normally be taxed more highly. In such cases unlawful dilution or substitution of a more highly taxed fuel with the low-taxed fuel may be detected by analysis of the highly taxed fuel to determine whether the tracer is present. Therefore in these cases, it is highly beneficial to use a tracer compound in the low-taxed fuel which is not easily removed, or laundered, from the fuel to a level at which it can no longer be detected. We have found that compounds of Formula I are resistant to removal from hydrocarbon fuels by several known methods of fuel laundering.

Preferably, when any one of $R^1$-$R^4$ is a halogen or halogenated alkyl group, the halogen atom is selected from bromine or fluorine and the halogenated alkyl group is a bromoalkyl or fluoroalkyl group. The halogenated alkyl group(s) may be partially or fully halogenated, linear or branched, acyclic or cyclic aliphatic groups. Preferred halogenated alkyl groups include trifluoromethyl, 1,1-difluoroethyl, fluoroallyl, heptafluoropropyl, tridecafluorohexyl, heptadecafluorooctyl. Most preferably at least two of $R^1$-$R^4$ in Formula I consist of a halogen atom or a halogenated alkyl group.

Alkyl group substituents may be straight chain or branched acyclic or cyclic aliphatic groups, preferably consisting of 4-12 carbon atoms. Branched or cyclic aliphatic groups are preferred. Preferred groups include tert-butyl, 1,1-dimethylpropyl, 2,2-dimethylpropyl (neo-pentyl), 1,1-dimethylbutyl, 1-ethyl-1-methylpropyl, 2,2-dimethylbutyl, 1,1,2-trimethylpropyl, 1,2,2-trimethylpropyl, 1-ethyl-2,2-dimethylpropyl, 1-methylethyl-2,2-dimethylpropyl, 1,1,3,3-tetramethylbutyl, cyclopentyl, cyclohexyl, 2-methylcyclohexyl, 3-methylcyclohexyl, 4-methylcyclohexyl, 2-ethylhexyl, 1-adamantyl, 2-adamantyl and decahydronaphthyl groups. Particularly preferred alkyl group, or haloalkyl group, substituents contain quaternary substituted carbon atoms, such as tertiary butyl.

It is preferred that none of $R^1$-$R^4$ includes fused aromatic rings such as naphthyl or anthracenyl, saturated heterocycles where the heteroatom is anything other than oxygen, unsaturated heterocycles, amino, imino, N-oxide, nitro, hydroxyl, carboxyl, ester, amide, acetal, thiol, thiol ethers, disulfides, sulfoxide, sulfone, sulfonate, phosphite ester, phosphate ester, cationic, anionic or zwitterionic groups; or metal containing substituents. It is possible, however, to use a molecule containing one of the above unpreferred groups provided that sufficient halogen, halogenated alkyl or bulky alkyl groups of the preferred type are present in the molecule to provide resistance to laundering.

Preferred tracer compounds in one embodiment have $R^1$-$R^4$ each selected from the group consisting of a bromine or fluorine atom; a partially or fully halogenated alkyl group; a branched or cyclic $C_4$-$C_{20}$ alkyl group; an aliphatic substituent linking two positions selected from $R^1$-$R^4$ in Formula I to one another; or a phenyl group substituted with a halogen atom, an aliphatic group or halogenated aliphatic group. Suitable tracer compounds include bis(3,5-bis trifluoromethyl-phenyl)-diazene, bis(3,5-bis t-butyl-phenyl)-diazene, bis(3-t-butyl, 5-trifluoromethyl-phenyl)-diazene, and (3,5-di-trifluoromethyl-phenyl)-(3,5-di-t-butylphenyl)-diazene.

Preferred tracer compounds have a boiling point greater than 100° C., especially greater than 140° C. at normal atmospheric pressure. A higher boiling compound is more difficult to remove by evaporation techniques including aeration by stirring or sparging air through the marked fuel. Preferably the tracer compound has a boiling point within the distillation range of the hydrocarbon liquid or within 10° C. of the boiling point of the hydrocarbon liquid, Preferably the tracer compound has a boiling point which is within the distillation range of the hydrocarbon liquid to be marked. More preferably, the tracer compound has a boiling point which is within the central 90% of the distillation range of the hydrocarbon liquid to be marked. Diesel has a boiling range from 180-390° C. Gasoline has a boiling range from 25-215°. When a hydrocarbon liquid which has a boiling range, such as diesel or gasoline, is to be marked, then a tracer compound having a suitable boiling point would be selected based upon the boiling range of the liquid. When a hydrocarbon having a defined boiling point, such as hexane, is to be marked then the tracer compound is preferably selected to fall within 10 degrees of the boiling point of that hydrocarbon liquid. The tracer compound is a liquid at room temperature or it is a solid which is soluble in the quantities at which it is to be used either in the liquid or in a master-batch formulation.

The tracer compound is added to the hydrocarbon liquid in such an amount as to provide a concentration of the tracer compound which is detectable by readily available laboratory methods capable of identifying the tracer compound in the liquid at the concentrations used. Suitable methods include, but are not limited to, gas chromatography coupled with a suitable detector such as an electron capture detector or a mass spectrometer, or spectrophotometric or colorimetric analysis, especially UV-visible (UV/vis) spectrophotometry. The hydrocarbon liquid may be identified as a hydrocarbon liquid containing the tracer by comparing the spectrum or other form of analytical result obtained from analysing the sample with a spectrum or result obtained from analysing a standard sample of a known hydrocarbon liquid containing a known concentration of the tracer. The sample result or a characteristic feature of the result, such as a peak area, may be compared with a value for a corresponding result or characteristic of a standard sample which is held in a memory of a data processing device. Alternatively the result from the sample may be interpreted without referring to a known standard result or sample.

Typically, the concentration of tracer in the liquid is within the range from 1 ppbv (part per billion by volume) to 100 ppbv, the actual amount used depending on the detection method and limit of detection of the particular tracer compound used. The tracer compound may be present at a higher concentration than 100 ppbv, for example up to 500 ppbv or even up to 1 ppmv (part per million by volume), although when the product to be marked is a high-volume commodity such as a motor-fuel, economic considerations usually favour lower levels of tracer compound. The tracer compound may be supplied and added to the hydrocarbon liquid, in the form of a concentrated dosing solution (or masterbatch) of the tracer compound in a solvent.

In this case the preferred solvent is a liquid which is similar to the liquid to be marked, although a different solvent, e.g. a hexane or mixed paraffins solvent may be used provided the presence of such a solvent can be tolerated in the hydrocarbon liquid to be marked. The concentrated dosing solution can be added to the hydrocarbon liquid to be marked so as to produce the required final concentration of the tracer compound by dilution. More than one tracer compound may be added to the liquid.

The selected tracer compound(s) is resistant to laundering by adsorption on activated charcoal or clay. In a preferred embodiment, at least 50% (more preferably at least 60%, especially at least 80%) of the tracer compound is retained in the hydrocarbon liquid after a sample of the liquid containing the tracer compound has passed through a column of fresh activated charcoal. The test to be applied for resistance to laundering by adsorption on a solid adsorbent is described below. Preferably at least 50% (more preferably at least 60%, especially at least 80%) of the tracer compound is retained in the hydrocarbon liquid after a sample of the liquid containing the tracer compound has passed through a column of fresh sepiolite clay.

Preferably the selected tracer compound(s) is resistant to laundering by chemical treatment with an acid or a base. In preferred embodiments, at least 50% (more preferably at least 75%) of the tracer compound is retained in the hydrocarbon liquid after a sample of the liquid containing 10-15 ppbv of the tracer compound has been vigorously agitated in contact with 10% aqueous HCl. Preferably at least 50% (more preferably at least 75%) of the tracer compound is retained in the hydrocarbon liquid after a sample of the liquid containing 10-15 ppbv of the tracer compound has been vigorously agitated in contact with 10% aqueous $H_2SO_4$. Preferably at least 50% (more preferably at least 75%) of the tracer compound is retained in the hydrocarbon liquid after a sample of the liquid containing 10-15 ppbv of the tracer compound has been vigorously agitated in contact with 10% aqueous NaOH. Preferably at least 50% (more preferably at least 75%) of the tracer compound is retained in the hydrocarbon liquid after a sample of the liquid containing 10-15 ppbv of the tracer compound has been vigorously agitated in contact with methanolic KOH (3M aqueous KOH diluted 1:10 in methanol). The test procedure for resistance to laundering by these chemical treatments is described below.

The invention will be further described in the following examples. In the Examples, the test methods which are used are described below. The meaning of ppb v/v is parts per billion based on the volume of liquid tracer compound in the total volume of liquid. In the following tests, T1 is bis(3,5-bis trifluoromethyl-phenyl)-diazene.

Test for Resistance to Removal by a Solid Adsorbant (Charcoal, Clay or Silica Gel)

A 30 cm long chromatography column, having an inside diameter of 1 cm, is filled with the solid adsorbent to a depth of about 15 cm. The adsorbent is supported in the column on a glass frit. 15 ml of a diesel fuel containing 10 ppb v/v of the test tracer compound is added to the column and allowed to percolate through the adsorbent bed under gravity. The liquid eluting from the column is collected, sealed into an autosampler vial and analysed immediately by gas chromatography-mass spectrometry (GC-MS). The amount of tracer detected in the collected liquid is reported below in Table 1, as a percentage of the original concentration.

The adsorbents used were:
Charcoal:—a powdered activated Norit™ charcoal (type RBAA-3) from Fluka (product number 29238),
Sepiolitic clay: a pure fine sepiolite clay from RS Minerals The above test procedure was carried out using 50 ml of diesel fuel marked with 10 ppb v/v of the tracer compound and the eluted liquid was collected in an open beaker before being passed through a second column packed with fresh adsorbent. The liquid from the second column was collected in an open beaker before being passed through a third column packed with fresh adsorbent. A sample of the liquid collected from each column was taken for analysis by GC-MS and the concentration of the tracer in the eluted liquid is shown in Table 1 as a percentage of the original concentration. When the concentration is greater than 100%, it is believed that the diesel fuel was retained on the adsorbent in preference to the tracer so that the solution became more concentrated.

TABLE 1

| Tracer | Sepiolitic clay | | | Charcoal | | |
|---|---|---|---|---|---|---|
| compound | 1st pass | 2nd pass | 3rd pass | 1st pass | 2nd pass | 3rd pass |
| T1 | 98 | 93 | 87 | 102 | 111 | 112 |

Test for Loss of Tracer Compound on Standing 1 ml of diesel fuel marked with 10 ppb v/v of the test tracer compound was placed in an open topped 2 ml autosampler vial, and repeatedly analysed by GC-MS over the course of one day after standing in normal laboratory conditions to determine the concentration of the tracer compound in the diesel. The samples were interspersed with sealed calibration standards to correct for any instrument drift over the period of analysis. The concentration of the tracer in the liquid is shown in Table 2 as a percentage of the original concentration. When the concentration is greater than 100%, it is believed that the diesel fuel evaporated more quickly than the tracer so that the solution became more concentrated.

TABLE 2

| | T1 |
|---|---|
| Concentration of tracer after 24 hours (%) | 104 |

Test for Resistance to Removal by Chemical Treatment

A quantity of the diesel fuel marked with 13 ppb v/v of the test tracer compound was shaken vigorously with an equal volume of a chemical agent selected from 10% HCl in deionised water, 10% H₂SO₄ in deionised water, 10% NaOH in deionised water and methanolic KOH (3M aqueous KOH diluted 1:10 in methanol). The mixture was allowed to settle, then shaken for a further minute before settling again. A sample of the diesel layer was analysed by GC-MS and the concentration of the tracer in the treated diesel liquid is shown in Table 3.

TABLE 3

| Tracer compound | 10% HCl | 10% H₂SO₄ | 10% NaOH | KOH/MeOH |
|---|---|---|---|---|
| T1 | 94 | 94 | 89 | 84 |

COMPARATIVE EXAMPLE

The compound shown below, corresponding to "Dye 7" of EP 1580254, was made according to the following procedure.

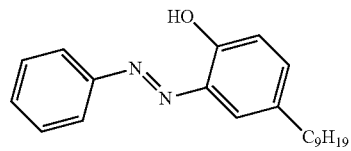

Aniline (1.517 ml) was added to a beaker containing hydrochloric acid (2 ml) and de-ionised water (10 ml). The mix was then placed into an ice bath and cooled to <5° C. Once the mix was cold enough, a solution of sodium nitrite (1.808 g) in water (20 ml) was prepared and added to the aniline mix slowly over 10 minutes, keeping the temperature below 5° C. The mixture was then left to stir in an ice bath for 30 minutes. After 30 minutes, sulfamic acid (1.62 g) was added to the mixture. A solution of nonylphenol (3.68 g) in toluene (20 ml) was added to the reaction mix and stirred vigorously. A solution of sodium acetate (20 g) in water (100 ml) was added to the reaction mix as a buffer over 30 minutes ensuring that it was kept cold. The mixture was then left to stir for another 5 hours and allowed to warm in the process.

The reaction mix was then added to a separating funnel and diluted with toluene (20 ml). The mixture was shaken and then left to settle. The organic phase was then washed with de-ionised water (100 ml) three times. It was then dried over anhydrous magnesium sulphate and the solvent removed on a rotary evaporator yielding a dark yellow oil.

A 10 mg/L solution of the prepared comparative dye was prepared in a synthetic test fuel, made by mixing together 76% iso-octane, 16% toluene, 5% t-butyl methylether and 3% ethanol (all quantities vol/vol). 10 ml of synthetic test fuel marked with the test tracer compound was shaken vigorously for 1 minute with 0.5 g of activated charcoal (decolourising) obtained from Sigma Aldrich (product number 161551). The mixture was allowed to stand for 1 minute and then shaken for a further minute before being filtered to remove the adsorbent. A sample of the fuel was analysed by UV/Vis spectrophotometry and the percentage of the tracer remaining was calculated.

This test procedure was repeated for a sample of the synthetic fuel containing bis(3,5-bis trifluoromethyl-phenyl)-diazene (T1), with the analysis of the sample being made by GC-MS because T1 is not susceptible to detection by UV/vis. Both results are shown in Table 4. The test shows that T1 is more resistant to removal by shaking with activated charcoal than the comparative example containing a phenolic moiety described in EP1580254.

TABLE 4

| Tracer compound | % of original concentration remaining after treatment with activated charcoal |
|---|---|
| Dye 7 of EP1580254 | 16% |
| T1 | 87% |

The invention claimed is:

1. A method of marking a hydrocarbon fuel or octane comprising the step of adding to said hydrocarbon fuel or octane, as a tracer compound in an amount of 1 ppbv to 1 ppmv of said hydrocarbon fuel or octane, a compound of Formula I:

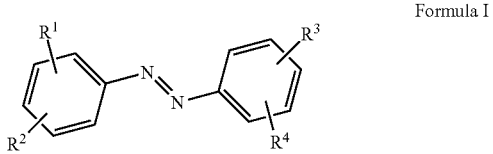

Formula I wherein at least one of $R^1$-$R^4$ is selected from a group consisting of:
 i. a bromine or fluorine atom;
 ii. a partially or fully halogenated alkyl group;
 iii. a branched or cyclic $C_4$-$C_{20}$ alkyl group;
 iv. an aliphatic substituent linking two positions selected from $R^1$-$R^4$ in Formula I to one another; and
 v. a phenyl group substituted with a halogen atom, an aliphatic group or halogenated aliphatic group;
and further wherein none of $R^1$-$R^4$ consists of a hydroxyl group or an amino group.

2. The method according to claim 1, wherein, when any of $R^1$-$R^4$ is a halogen or halogenated alkyl group, the halogen atom is selected from bromine or fluorine and the halogenated alkyl group is a bromoalkyl or fluoroalkyl group.

3. The A method according to claim 1, wherein at least two of $R^1$-$R^4$ in Formula I consist of substituents selected from the group consisting of fluorine, bromine and a halogenated alkyl group.

4. The method according to claim 1, wherein none of $R^1$-$R^4$ in Formula I contains fused aromatic rings, saturated heterocycles where the heteroatom is anything other than oxygen, unsaturated heterocycles, amino, imino, N-oxide, nitro, hydroxyl, carboxyl, ester, amide, acetal, thiol, thiol ethers, disulfides, sulfoxide, sulfone, sulfonate, phosphite ester, phosphate ester, cationic, anionic or zwitterionic groups; or metal containing substituents.

5. The method according to claim 1, wherein, in Formula I, each $R^1$-$R^4$ is selected from the group consisting of a bromine or fluorine atom; a partially or fully halogenated alkyl group; a branched or cyclic $C_4$-$C_{20}$ alkyl group; an aliphatic substituent linking two positions selected from $R^1$-$R^4$ in Formula I to one another; and a phenyl group substituted with a halogen atom, an aliphatic group or halogenated aliphatic group.

6. The method according to claim 1, wherein the tracer compound is selected from the group consisting of bis(3,5-bis trifluoromethyl-phenyl)-diazene, bis(3,5-bis t-butyl-phenyl)-diazene, bis(3-t-butyl, 5-trifluoromethyl-phenyl)-diazene, and (3,5-trifluoromethyl-phenyl)-(3,5-di-t-butylphenyl)-diazene.

7. A method of identifying a hydrocarbon fuel or octane comprising the steps of marking said hydrocarbon fuel or octane by the method of claim 1, and subsequently analysing a sample of a hydrocarbon fuel or octane for the presence of said tracer compound to determine whether said sample is a sample of said marked hydrocarbon fuel or octane.

* * * * *